United States Patent
Thompson et al.

[11] Patent Number: 5,817,505
[45] Date of Patent: Oct. 6, 1998

[54] PARTICLE SETTLER FOR USE IN CELL CULTURE

[75] Inventors: Keith John Thompson, Edinburgh; James Samuel Wilson, Midlothian, both of Great Britain

[73] Assignee: Bioscot Limited, Edinburgh, Great Britain

[21] Appl. No.: 545,712

[22] PCT Filed: May 9, 1994

[86] PCT No.: PCT/GB94/00997

§ 371 Date: Nov. 7, 1995

§ 102(e) Date: Nov. 7, 1995

[87] PCT Pub. No.: WO94/26384

PCT Pub. Date: Nov. 24, 1994

[30] Foreign Application Priority Data

May 7, 1993 [GB] United Kingdom .................... 9309429

[51] Int. Cl.[6] .......................... C12M 3/00; B01D 33/06; B01D 12/00; B01D 21/00
[52] U.S. Cl. .................................. 435/286.1; 435/289.1; 435/308.1; 435/813; 210/373; 210/394; 210/521; 210/802
[58] Field of Search ............................ 435/286.1, 289.1, 435/308.1, 819, 813; 210/800, 801, 802, 513, 521, 383, 393, 394

[56] References Cited

FOREIGN PATENT DOCUMENTS

WO 94/11312  5/1994  WIPO.

OTHER PUBLICATIONS

Bioprocess Engineering, (May 1993) vol. 9, No. 2–3, pp. 91–96, May 1993.
Biotechnology and Bioengineering, vol. 41, No. 3, pp. 361–369, Feb. 5, 1993.

*Primary Examiner*—David A. Redding
*Attorney, Agent, or Firm*—Sterne, Kessler, Goldstein & Fox P.L.L.C.

[57] ABSTRACT

Disclosed is a device for separating particles from a bulk liquid, such as viable hybridoma cells from antibody-containing liquid medium. The device comprises a plurality of settlement plates, or other surfaces, being inclined to the vertical, and a pump or other means for causing liquid containing the particles to flow upwardly over the surfaces at such a rate as to allow particles to be separated from the bulk liquid to form sediment layers on the surfaces and slide down them for collection at an appropriate point.

31 Claims, 4 Drawing Sheets

PARTICLE SETTLER FOR USE IN CELL CULTURE

BACKGROUND OF THE INVENTION

1. Field of the Invention

This invention relates to a particle settling device and to the use of such a device in cell culture. The invention has application in the culture of animal cells for the production of secreted substances such as polypeptides and proteins, particularly monoclonal antibodies.

2. Description of Related Art

Over recent years there has been considerable interest in the culture of animal cells for the production of a variety of useful products. Cell fusion technology (Köhler and Milstein, Nature 256 495–597 (1975)) has allowed the creation of many different hybridomas secreting murine monoclonal antibodies with a range of specificities. Monoclonal antibodies have proved useful as therapeutic and diagnostic agents, for immunopurification, and as research tools. Human monoclonal antibodies have also been produced from cell fusion processes (Thompson et al, Immunology 58 157 (1986)), further extending the range of utility. Recombinant DNA techniques have been used to alter and improve monoclonal antibodies, often still using a variety of animal cells as hosts. Recombinant DNA technology has also been used to create cell lines with foreign genes carried within capable of producing the product encoded by that gene. The animal cell has often been found to be superior to bacteria or yeast as a host for protein expression because of the animal cell's ability to glycosylate protein and to carry out post-translational modification.

Thus the technologies of animal cell fusion and recombinant DNA technology in animal cells are playing an important role in the production of useful products, in addition to their traditional role in vaccine production.

In order to make these products in sufficient quantity at an economic cost, cell culture processes have to be scaled up. Traditional batch fermentation technology has relied upon stirred tank or airlift fermenters. Several examples of large fermenters (for example, 2000 dm$^3$ airlift fermenters) exist already. Such fermenters have to be housed in large buildings and need a supply of utilities. Downstream processing of the output, which is often relatively low, is usually required.

There has been much interest in continuous perfusion technology whereby cells are retained within the fermenter whilst cell-free supernatant containing product is continuously withdrawn and the fermenter is continuously replenished-with fresh medium for a period of weeks or months. This allows the achievement of higher cell densities within the fermenter, potentially resulting in high substrate-to-product conversion rates and better use of fermenter time; additionally, smaller fermenters can be used. In order to achieve cell retention then there must be some means of physically retaining the cell within the fermenter, ultimately separating the cell from the surrounding medium which then becomes the product stream. As animal cells have no cell wall and are sensitive, this retention means must be gentle. The device or method used for this purpose must be capable of substantially continuous sterile operation without significant breakdown or process interruption. The design should be simple, robust, sanitary and capable of economic scale up. It should also be capable of containment should hazardous organisms be required to grow within it.

A variety of devices or methods have been proposed or put into use to achieve cell retention. These include external or internal spin filters (Himmelfarb et al, Science 164 555–557 (1969)), membrane separators (Knazek et al, Science 178 65–67 (1972)), cell entrapment (Nilsson et al, Nature 302 629–630 (1983)), encapsulation (Jarvis and Grdina, Bio Techniques 1 22–27 (1983)) or gravitational settling (Kitano et al, Appl. Microbiol. Biotechnol. 24 282–286 (1986) and Batt et al, Biotechnol. Prog. 6 458–464 (1990)).

Most devices currently employed have been operated successfully at the laboratory scale and some at the industrial scale; however, they all suffer from some drawbacks. Spin filter devices are prone to clogging, rely on mechanical seals, and are prone to breakdown or loss of integrity. Membrane devices are prone to fouling, requiring repeated replacement during a run with the attendant aseptic risk. Membrane devices also require a high tangential flow rate to keep the membrane clean, which can present problems to shear-sensitive cells.

Cell encapsulation technology often results in low viability within the capsule and the antibody is retained within. The formation of the capsules is a complex process that can be difficult to scale up successfully. Cell entrapment in beads of substances such as agarose or alginate may suffer from the disintegration of the beads on extended culture, again presenting scale up problems.

Gravitational settling devices have great potential as they can be simple in construction and have no moving parts that would break. As they have no filters or membranes it is impossible for them to clog or block in normal use. The use of a settling tank is a simple way of achieving this whereby cell suspension is allowed to rest in the tank and cells settle to the bottom leaving a cell-free top layer. The main disadvantage for this type of tank is that it is large in relation to the fermenter to which it is attached and the residence time for cells inside is long, leading to deleterious metabolic effects. The metabolic effects can be overcome by cooling the tank; however, the size of the tank is still problematical even allowing for improvements in design such as in the Dortmund Settler (Hulscher et al, Biotechnology and Bioengineering 39 442–446 (1992)).

The theory of inclined sedimentation was developed in 1925 by E Pounder, (J. Exp. Physiol. 15 235–253 (1925)) through studies of sedimentation and rouleaux formation of erythrocytes. It has been widely applied in biomass recycling but only recently in animal cell culture. In its simplest form, cells are removed from suspension by settling onto the upward facing slope of a long tube or channel inclined from the vertical. Here they form thin sediment layers that slide down to the bottom of the vessel. Thus the cells are concentrated at the bottom and supernatant is clarified at the top. The concentrated cells are returned to the fermenter thus keeping cells within the fermenter and the clarified supernatant containing the secreted molecule is withdrawn from the top as a harvest.

In general the theory of inclined sedimentation can be summarised by the equation presented by Batt et al, (Biotechnol. Prog. 6 458–464 (1990)) where:

$$S(v) = vw(l\sin\theta + b\cos\theta)$$

where

S(v) is the volumetric rate of clarified fluid
v is the particle settling velocity
w is the width of the settler plate
l is the length of the settler θ is the angle of inclination to the vertical b is the spacing between the inclined walls of the settler From this equation it is possible to predict the performance characteristics of a settling device for particles of various sedimentation velocities, for example non-viable hybridomas at 1.1 cm/hr, and viable hybridomas at 2.9 cm/hr.

All the devices designed or tested to date have only been applied on a very small scale. These devices could not be scaled up volumetrically because an increase in size would cause a proportional increase in cell residence time to allow use at an industrial scale.

It has now been discovered that by a change in design to sedimentation settlers it is possible for such settlers to be scaled up in size. The design change which enables this is to provide more than one sedimentation surface.

SUMMARY OF THE INVENTION

According to a first aspect of the present invention, there is provided a device for separating particles from a bulk liquid, the device comprising means defining a plurality of settlement surfaces, the surfaces being inclined to the vertical, and means for causing liquid containing the particles to flow upwardly over the said surfaces at such a rate as to allow particles to be separated from the bulk liquid to form sediment layers on the surfaces and slide down them. The particles so separated may then be collected, recycled disposed of or otherwise subjected to further processing and/or handling, depending on the particular application.

Such a "multi lamellar" settling device is capable of being compact, of conforming to the principles of sterile design, of being scaled up and of being able to operate continuously. Devices in accordance with the invention are therefore capable of meeting the stringent demands of animal cell culture, accomplishing cell retention and high productivity. They are also capable of being used as devices for clarification whereby particles are partitioned and retained from a bulk liquid flow containing such particles.

By their design, settling devices in accordance with the invention present a relatively large surface area (compared to known devices), defined by the plurality of the settlement surfaces, to the bulk liquid.

A device in accordance with the invention is expected to have many applications, but one of the most common will be in continuous fermentation of cells, particularly of animal origin. The device may be connected to the outlet of a fermenter to remove either all cells from the cell supernatant liquid or a selected population of cells (for example non-viable cells, which have different sedimentation characteristics from viable cells). The invention has particular application in the fermentation of protein-producing cells, including cultured hybridomas excreting monoclonal antibodies.

It is preferred that the device comprise at least three, five, ten or even fifteen settlement surfaces to accommodate a variety of sizes of settlement areas. Greater flexibility is achieved if some, or preferably all, the means defining the surfaces are removable.

The surfaces will in most embodiments of the invention be parallel to one another, as the settlement characteristics of each surface will then be similar if not identical. Occasionally, though, it may be desirable for at least one of the plates to be slightly convergent (or divergent) from the other or others, so as to provide different sedimentation characteristics on certain surfaces, for example to cater for differences in flow over the various surfaces which may arise, for example, from the site of the liquid inlet.

The means defining the settlement surfaces are preferably plates, with uppermost surfaces (on which the sedimentation and sliding take place) adapted for the purpose. Mirror-polished stainless steel provides an excellent surface. If necessary or desirable, especially when using less costly (and less effective) surfaces than mirror-polished stainless steel, the surfaces can be coated with an appropriate lubricant, such as a silicone material; dimethyldichlorosilane is an example. The plates may be arranged in a stack, which is removable; in another embodiment, individual plates or combinations of plates are removable.

The angle at which the surfaces, and the plates themselves in the preferred embodiments of the invention, are inclined to the vertical will be determined according to the particular implementation of the device.

Generally, the angle will be from 10° to 50° or even 80°, but for many applications it will be from 20° to 40°, or about 30°. Preferably, means are provided to allow the angle of inclination to be adjusted. Such means may be an adjustable leg or stand.

The angle of inclination is one of the parameters that is set depending on the separation task that the device is to carry out. It will be appreciated that a bulk liquid may contain a heterogeneous population of particles, only some of which are desired to be removed. Particles of different densities and diameters will sediment at different rates, and so the parameters of the device, including the angle of inclination, can be set so as to remove only the unwanted particles. For example it may be desired to remove particles having sedimentation rates of greater than 0.1 cm/h or from 0.01 to 10 cm/h; in the application of the invention to hybridoma technology, it may be desired to separate viable from non-viable cells.

Other parameters include the liquid flow rate and the surface length (in the direction of flow). The liquid flow rate will depend entirely on the particular application of the device. In the case of the separation of hybridoma cells from cell supernatant liquid, where the cells are to be retained in the reactor system, the flow rate of cell-containing liquid from an attached fermenter over the surfaces and back to the fermenter will often be from 0.5 to 5 dm$^3$/h and is preferably about 1 dm$^3$/h. This rate can be varied according to cell type; a primary requirement is that the cells be returned to the fermenter at a sufficient rate to prevent substantial cell settling in the flow and return pipework.

The length of the surfaces, in the direction of flow, can be varied as desired. Sizes from 5 cm to 30 cm are common. For maximum retention of both viable and non-viable hybridoma cells, a long length such as about 30 cm can be chosen. For maximum discrimination between viable and non-viable hybridoma cells, shorter lengths such as about 10 cm are more appropriate. In general, the shorter the length is, the lower the overall settling efficiency will be, but the settler will have greater ability to discriminate between viable and non-viable (ie, dead) cells.

The spacing between plates can be any convenient distance, usually between 0.2 cm and 2 cm, inclusive. For hybridoma separation, about 0.5 cm appears to allow optimum flow of supernatant liquid and cell settlement. The equation of Batt et al. quoted previously can be modified, as follows, to take into account the spacing between plates in a device in accordance with the invention:

$$S(v) = vnw(l \sin\theta + b \cos\theta)$$

where

S(v) is the volumetric rate of clarified fluid v is the particle settling velocity n is the number of plates w is the width of the settler plate l is the length of the settler plate θ is the angle of inclination to the vertical b is the spacing between the plates.

This modified equation may be used to produce dimensions for devices in accordance with the invention for many different applications, and for various numbers of surface-defining plates in a given application. Large or small scale devices may be designed accordingly: large versions will tend to have more and/or wider plates.

The plates or other means defining the surfaces will usually be contained in a housing; this will probably be critical when the device is to work aseptically. The housing may be of rectangular section and can be constructed from any appropriate material; stainless steel, which may be electropolished, is suitable for many applications, including sterile ones. The housing may be sized to contain a greater number of plates than are required in a given application; in such a case, a box member may be provided (preferably constructed of mirror-polished stainless steel, like the plates) to occupy the space left by the missing plates, thereby to preserve plate separation.

Liquid containing the particles to be separated will enter the housing through an inlet; in a sterile design, the inlet will have a sanitary connector. The inlet will generally be located at, below or not far above the bottom of the settlement surfaces, for maximum use to be made of their length along the direction of flow.

Liquid from which unwanted particles have been removed will leave the housing through an outlet, which may similarly be provided with a sanitary connector. The outlet will generally be located at, above or not far below the top of the settlement surfaces, again to maximise the use that is made of the length of the settlement surfaces.

At the lowermost point of the housing which can be reached by sedimented particles sliding down the surfaces may be provided a collection outlet for the particles. The collection outlet may facilitate return of the particles to another apparatus (for example a fermenter) to which the device is attached or otherwise operatively coupled.

The means for causing the liquid to flow upwardly over the settlement surfaces may be a pump (for example a peristaltic pump), although a gravity fed system could readily be implemented if desired.

The pump, or other means causing the liquid to flow, may operate continuously or intermittently. If operated intermittently, during the period when the pump is off, settling occurs while the surrounding fluid is still. This allows those cells that have already settled to slide down the settling surfaces unhindered by the upward flow of liquid, as can happen during normal countercurrent operation. Intermittent operation has the advantage that it can improve the speed at which the cells return downwardly, thereby improving cell viability and productivity.

Alternatively or additionally, the flow of the liquid may be reversed, for example for periods of about one minute every five minutes. Periodic reversal, which may be achieved by reversing the direction of operation of a pump, has the effect of causing short periods of co-current settling and also of helping ensure more rapid downward return of those cells that have already settled, by virtue of the co-directional movement of liquid above them.

Temperature control means may be provided to keep the temperature of liquid in the device within predetermined limits. The limits will vary depending on the application and may be, for example, from 1° to 60° C. Usually, they will be between 20° and 40° C., and for warm blooded animal cell-containing liquids will be about 37° C. The temperature control means may comprise a water jacket or any other suitable arrangement.

As has been made clear, a device as described above can be coupled to a fermenter for cells. According to a second aspect of the present invention, therefore, there is provided a bioreactor apparatus, the apparatus comprising a fermenter vessel adapted to contain cells in liquid medium, and a device as described above, the device being so coupled to the fermenter vessel to allow cells, or a population of cells, in the liquid medium to be separated from liquid medium and returned to the fermenter vessel.

The fermenter vessel may be of any suitable suspension design (such as stirred tank or airlift). More than one settlement device may be connected in parallel (or even serially, if different settlement criteria are to be applied one after an other).

The fermenter may be adapted for culturing mammalian, other animal, plant or microorganism cells, whether genetically modified, immortalised, otherwise modified or unmodified. The invention is particularly applicable to the continuous perfusion fermentation of, for example, monoclonal antibody-secreting hybridoma cells.

According to a third aspect of the present invention, there is provided a process for separating particles from a bulk liquid, the process comprising causing liquid containing the particles to flow upwardly over a plurality of settlement surfaces, the surfaces being inclined to the vertical, at such a rate as to allow particles to be separated from the bulk liquid to form sediment layers on the surfaces and slide down them.

Preferred features of each aspect of the invention are as for each other aspect, *mutatis mutandis*.

Preferred embodiments of the invention will now be delineated, with reference to the accompanying drawings, in the following detailed description and examples.

DESCRIPTION OF THE PREFERRED EMBODIMENTS

Figure 1:
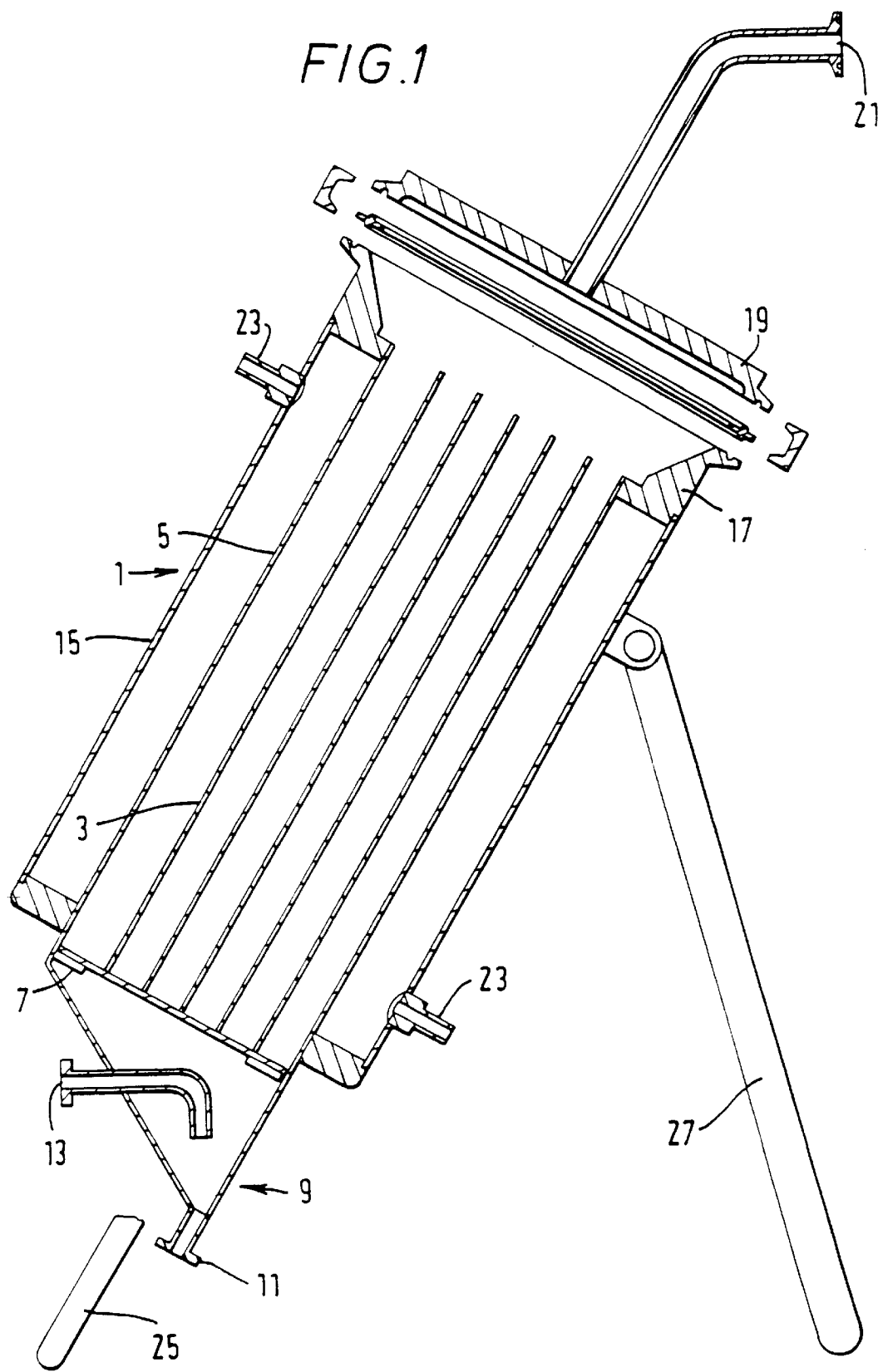
FIG. 1 shows a vertical sectional view through a separating device of the invention.

The general arrangement of a separating device 1 in accordance with the invention is shown in FIG. 1. The device 1 comprises a series of plates 3 welded together to form a rigid stack capable of insertion into a square chamber 5 which is inclined at 30° to the vertical. The square chamber 5 is a box section of a size to accommodate the standard plates with minimum clearances. The stacked plates 3 are retained within the box section by four lugs 7. The box section of the chamber 5 is drawn to a tapered bottom chamber 9; all the angles of the taper are 30° from the vertical, thereby mimicking the angle of inclination of the stacked plates. The tapered bottom chamber 9 terminates in a ½" (1.27 cm) OD tube with a TRI-CLAMP™ connector 11; this allows sanitary connection for return of recirculated and settled materials. An inlet 13 to the device is located in the bottom chamber 9 and connects the device 1 to the fermenter side of a recirculation loop. The inlet 13 is angled to direct the recirculation liquid flow path through the bottom chamber to the outlet connecter 11. As the settling motion can be disturbed by convection currents, the device 1 is provided with a water jacket 15 consisting of tube of greater cross-section than the square chamber 5. A transition piece 17 takes the square box section outlet to the round jacket. The transition piece 17 is provided with a 6" (15.27 cm) TRI-CLAMP connector to allow connection to a headplate 19 also provided with TRI-CLAMP connections. The headplate 19 has an outlet tube (½ or 1.27 cm OD) 21 with a TRI-CLAMP connector for the withdrawal of supernatant from which cells have settled. The outlet tube 21 can be connected to any suitable sterile collection tank.

The water jacket 15 is provided with hose connections 23 to facilitate the connection of the jacket to a thermocirculator to allow temperature control of the settler. The device 1 is provided with three legs, two fixed 25 and one which is both adjustable and removable 27. The adjustable leg 27 allows variation of the angle of inclination of the device 1, should it be necessary.

The device 1 is constructed entirely from 316L stainless steel. It can be fabricated by any engineering workshop proficient in the manufacture of small high quality stainless steel vessels used in biological or pharmaceutical industries. The welding should be finished to a high standard with all welds exposed to the cell suspension dressed and ground down. The plates 3 should be mirror-polished prior to welding together in a stack and all care taken not to scratch or damage the surface finish during construction. The rest of the vessel interior surfaces should be electro-polished to provide a smooth finish.

Figure 2:
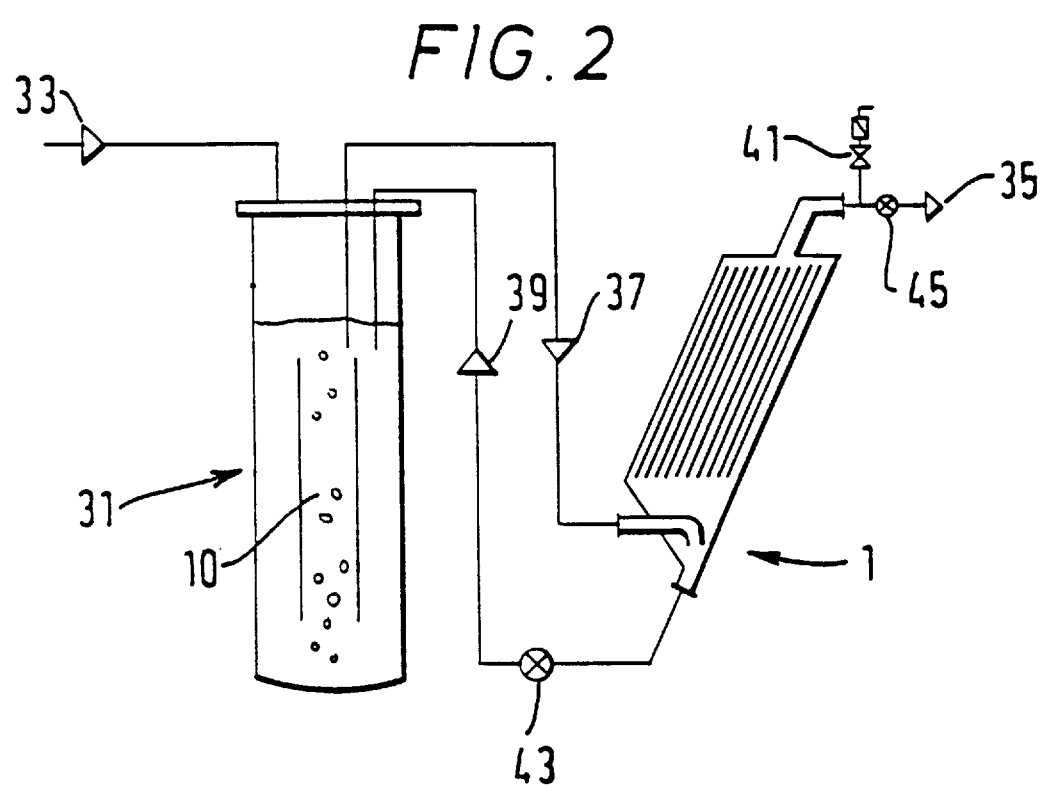
FIG. 2 shows schematically the attachment of the separating device of FIG. 1 to a 25 $dm^3$ fermenter.

In use, as indicated schematically in FIG. 2, a culture of mammalian cells should be inoculated into a fermenter 31 of approximate size, eg 10–30 dm$^3$ working volume, which contains a draft tube 10. The fermenter 31 should be capable of controlling dissolved oxygen levels, pH, temperature overpressure and mixing rate. The fermenter 31 should also be capable of continuous operation with a feed of fresh medium, fed through inlet 33, to balance the withdrawal of depleted, product containing medium via the settler at outlets 35. The fermenter 31 should be operated initially as if in batch mode until the cells are in mid-logarithmic phase of growth. The fermenter should be operated with a small overpressure of, for example, 0.2 BarG. At this point an external loop 37, 39 containing the separator device 1, with water jacket 15 previously equilibrated to the same temperature as the fermenter, should be slowly filled from the fermenter by venting the separating device 1 at valve 41. As the fermenter 31 is pressurised, the fermenter contents will fill the separating device 1. The fermenter 31 should be refilled to its working level with fresh medium from the fresh medium holding tank during the filling process.

The recirculation loop 37, 39, containing a recirculation pump 43, should be started to ensure continual passage of cells from the fermenter through the settler recirculation/return chamber. The system should then be allowed to equilibrate for a period of from 1 to 18 hours. This will ensure that the cell contents drawn into the settler will have settled. Perfusion can now be initiated by starting a harvest pump 45. Initially the perfusion rate should be no more than ½ vvd and then, according to cell growth and medium utilisation, can be increased until either the limits of the fermenter's ability to support cells (usually the $O_2$ transfer rate), or the settler's ability to retain cells, is reached.

The fermenter/settler system can then be operated for long periods, providing that a constant supply of fresh medium and a constant draw off can be maintained. With the recirculation pump 43 running at fixed speed the harvest pump 45 can be increased in speed and the flow from the fermenter to the settler will automatically compensate as the entire system is pressurised from the fermenter.

Alternatively, the pump can be pulsed on and off sequentially via a timing device, such that when the pump is on cell suspension is drawn over the settling plates, settling occurring in the normal countercurrent mode, as above. When the pump is turned off, settling occurs whilst the surrounding fluid is still. This also allows those cells that have already settled to slide down the settling plates unhindered by the upward flow of the liquid, as can happen during normal countercurrent operation. This technique can improve the speed at which cells return to the fermenter and thus improve cell viability and productivity.

A further refinement of this approach is periodically (eg is for 1 minute every 5 minutes) to reverse the flow of pump 45 thereby causing brief periods of co-current settling and also help ensure more rapid return to the fermenter of those cells that have already settled by the co-directional movement of liquid above them.

The device can also be used in many alternative modes for a variety of procedures including:

1. Single pass clarification of particle/cell containing liquids where settled particles/cells are not recirculated but particle/cells containing liquid enters the bottom of the settler and a particle/cell depleted stream is drawn off, particles/cells being retained in the bottom of the settler (for removal either intermittently or at the end of the process into a sump for further processing or killing).
2. The use of two or more settlers in series the first for the retention of viable cells for return to a fermenter. The second or subsequent larger settler being for the retention of all cells prior to further downstream processing.

Other embodiments include fifteen plate and ten plate devices 1. The main body of the settler can be identical in both cases with only the construction of the insert differing. The ten plate insert can thus be identical in all respects to the fifteen plate insert except that five plates are replaced by a watertight box (also mirror polished). The plate length for the ten plate insert is 10 cm.

EXAMPLE 1

Growth of Hybridoma Cells

Murine hybridoma cells from the cell line designated ES4 were cultured to obtain sufficient cells to inoculate a 25 dm$^3$ airlift fermenter (Chemap Zurich). These cells had been fused from mouse spleen cells and mouse myeloma cells in the usual manner, now well known in the art, and constituted an immortal cell line which, in culture, produced antibodies against human blood group B antigen.

The inoculum was prepared by thawing an ampoule containing approximately $10^7$ frozen cells and culturing in flasks at 37° C. in a mixture of DMEM/F12 (Gibco), plus 5% foetal calf serum. The culture was expanded serially in flasks to obtain sufficient cells to seed a 1 dm$^3$ spinner vessel with $10^5$ cells/ml in the above media. On further cell growth the 1 dm$^3$ spinner was used to seed a further spinner vessel with 4 dm$^3$ working volume. This 4 dm$^3$ spinner culture was used to inoculate the 25 dm$^3$ fermenter.

Initial cell density in the fermenter (day 0) was $0.7\times10^5$ viable cells/ml. The fermenter was controlled with temperature at 37° C., pH at 7.2 and dissolved oxygen (dO) at 50% of air saturation. Gas sparge rate was set to 20 dm³ of gas per hour. Gas contained air with oxygen, carbon dioxide and nitrogen blended into the total gas flow to maintain the preset control valves for pH and dO. The run was designated SAL 024.

Medium was again DMEM/F12 with 5% FCS. The working volume of the fermenter was 21 dm³. Cells were allowed to grow freely in batch mode for three days until the viable cell count reached $5\times10^5$/ml with a percentage viability of 86%.

A previously autoclaved separating device 1 (settler) was attached to the fermenter as shown in FIG. 2 with silicon tubing from the recirculation outlet and inlet to needle connectors (Chemap) for sterile connection to the fermenter; the settler jacket was filled and equilibrated at 37° C. to match the fermenter temperature. The settler was slowly filled with the contents of the fermenter by venting trapped air from the settler. The volume of culture lost from the fermenter into the settler was replaced automatically by a medium feed system with fresh medium (DMEM/F12 5% FCS). The recirculation pump 43 was started and the whole system allowed to equilibrate for 2 hours to allow settling and return of cells introduced into the settler.

Clarified liquid was drawn off the settler at an initial rate of 10 dm³ per day (the perfusion rate as volumes withdrawn per volume of fermenter per day). This was progressively increased over a period of nine days to a maximum of 50 dm³ per day.

Viable cell mass rose to approximately $5\times10^6$ cells/ml after twelve days (coinciding with 50 dm³/day perfusion rate). This stayed relatively constant for a further ten days. Total cell numbers (viable plus dead cells) rose sharply from day twelve to day fifteen and then less sharply thereafter.

Figure 3:
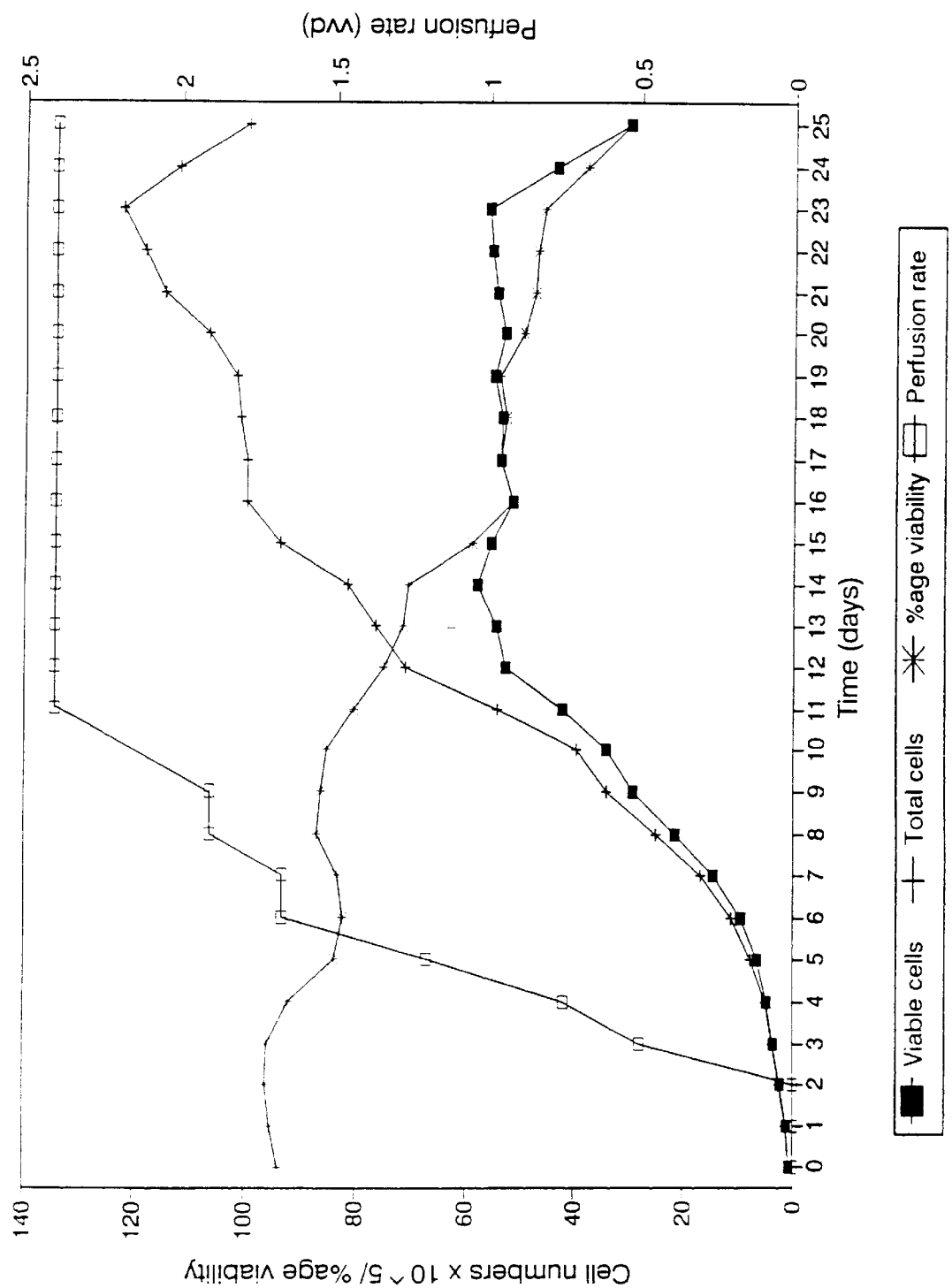
FIG. 3 shows the variation of total and viable cell numbers, percentage viability and perfusion rate with time in the course of the experiment conducted in Example 1.

A constant viable cell mass was therefore maintained with rising total cell mass and declining percentage viability. This was maintained until day twenty-two when problems with the control of the fermenter set points brought about a decline on the viable cell population and thereafter a termination of the run. Results are shown in FIG. 3.

A total of 935 dm³ of medium were used. The initial 100 dm³ was DMEM/F12 5% FCS and the subsequent medium was DMEM/F12 2% FCS. This yielded a total of 34.9 grammes of antibody.

Throughout the experiment the settler retained 95–99% of cells. Typically there were $0.5\times10^5$ viable cells with $2\times10^5$ dead cells in the settled offtake. This represents 99% viable cell retention and 96% dead cell retention.

EXAMPLE 2

Figure 4:
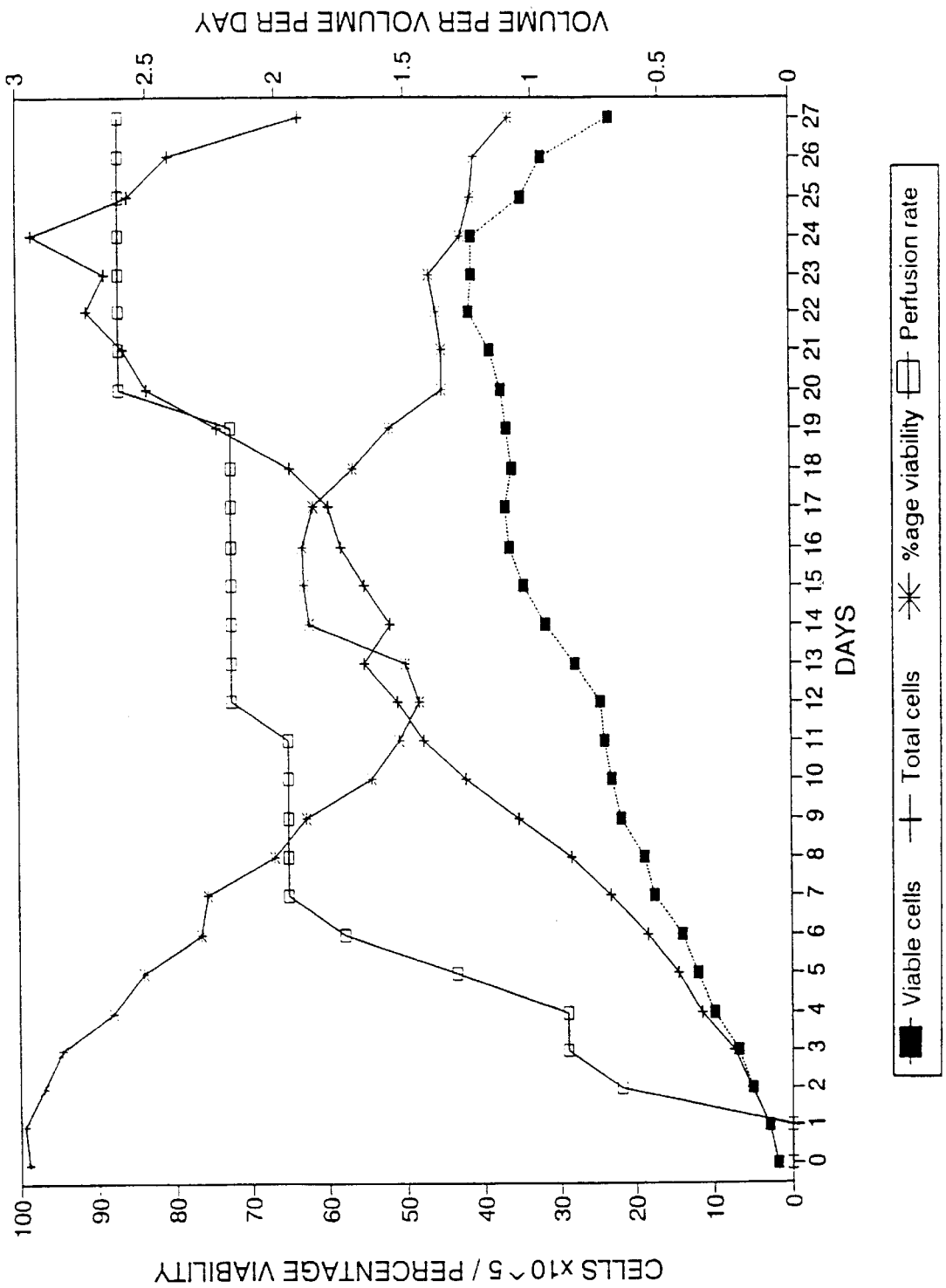
FIG. 4 shows the variation of total and viable cell numbers, percentage viability and perfusion rate with time in the course of the experiment conducted in Example 2.

All operating conditions (with the exception of perfusion rate) of Example 1 were repeated; the results are shown in FIG. 4. The run number was SAL 027.

EXAMPLE 3

Efficiency of Settler for Viable and Dead Cell Retention

A fermentation was established as for Example 2 but with the following modifications:

1. The cell line used was BIRMA 1, a murine hybridoma secreting antibody specific for blood group substance A.

2. After nine days post inoculation the perfusion rate was 50 dm³ per day and the cell population in the fermenter had stabilised at $3.76\times10^6$ viable and $5.08\times10^6$ total. (Total is the sum of viable and dead cells.) In the harvest stream there were $0.3\times10^5$ viable and $2\times10^5$ total cells, giving 99% viable cell retention and 96% total cell retention.

3. The perfusion rate was increased stepwise to test the retention efficiency of the settler (see table below for results).

| Perfusion Rate | | Cells in Fermenter × $10^5$ | | Cells in Harvest Stream × $10^5$ | | Retention efficiency % | | Time to stabilise before count taken |
|---|---|---|---|---|---|---|---|---|
| VVD | dm³/Day | Viable | Total | Viable | Total | Viable | Total | |
| 2.38 | 50 | 37.6 | 50.8 | 0.3 | 2 | 99.2 | 96 | NA |
| 2.86 | 60 | 37.6 | 50.8 | 0.3 | 2 | 99.2 | 96 | 48 hrs |
| 3.62 | 76 | 50.8 | 75.5 | 1 | 4.3 | 97.4 | 94 | 24 hrs |
| 4.38 | 92 | 20.5 | 50.5 | 0.4 | 4.1 | 98 | 92 | 48 hrs |
| 6.03 | 127 | 10.7 | 23.2 | 1.4 | 5.2 | 87 | 77 | 1 hr |
| 8.1 | 170 | 10.7 | 23.2 | 1.9 | 7.0 | 82 | 70 | 1 hr |

From the above results it can be seen that there was no effective increase in loss of cells per ml of harvest stream up to a perfusion rate of 4.38. For this fermentation the total loss of cells from the fermenter via the settler at a perfusion rate of 3.62 VVD would be $3.27\times10^{10}$. The total fermenter contents being $1.59\times10^{11}$ total loss of cells from the fermenter being 20%. The fermenter is able through cell growth to replace these lost cells.

At a perfusion rate of 4.38 VVD there is no significant increase in the percentage loss of cells per ml of settled material from the fermenter; however, the total cells lost per day increases due to the increased perfusion rate which is $3.8\times10^{10}$. The total number of cells in the fermenter was $1.06\times10^{11}$, representing a total loss of cells from the fermenter of 36%. Because there was a drop in both viable cell count and total cell count in the fermenter it was concluded that the fermenter was not replacing cells at the rate that they were being lost.

The perfusion rate was increased to 6.03 VVD and after 1 hour both the number of viable cells and total cells had increased in the harvest stream representing a loss of $6.6\times10^{10}$ per day against a fermenter with $4.87\times10^{10}$ cells total. This indicated that at this rate total cell washout would be rapidly achieved. A further increase in cell loss was observed at a perfusion rate of 8.1 VVD.

From these results for this size of settler used with a 21 dm³ airlift fermenter, the maximum perfusion rate is 76 dm³ per day (or 3.62 VVD). Experiments of this type can be used to deduce optimal configuration of settler size versus required perfusion rate.

EXAMPLE 4

Non-Viable Cell Breakthrough Examination

A fermentation was established as for Example 3 but with the following modifications:

1. The cell line used was NELP 3, a human heterohybridoma secreting antibody specific for blood group substance RhD.
2. The settler device was equipped with an insert of 15 plates each plate of 10 cm length by 10 cm width. With a sedimentation rate of 1.1 cm/hr for non-viable cells, a 10 cm plate was expected, according to the modified Batt equation, to show non-viable cell breakthrough above 21.5 dm$^3$ day exchange rate ie 1 VVD approximately.

The perfusion rate was increased stepwise to test the retention efficiency and breakthrough level of the settler (see table below for results).

| Perfusion Rate | | Cells in Fermenter 10$^5$ | | Cells in Harvest 10$^5$ | | Retention Efficiency % | |
|---|---|---|---|---|---|---|---|
| VVD | dm$^3$/Day | Viable | Total | Viable | Total | Viable | Total |
| 0.57 | 12 | 13.9 | 19.4 | 0.9 | 1.7 | 93.5 | 91.2 |
| 0.81 | 17 | 18.6 | 24.6 | 0.45 | 1.75 | 97.6 | 92.9 |
| 0.81 | 17 | 26.5 | 33.7 | 0.47 | 1.82 | 98.2 | 94.6 |
| 0.95 | 20 | 25.6 | 38.4 | 0.67 | 2.8 | 97.4 | 92.7 |
| 0.95 | 20 | 29 | 51.8 | 0.7 | 3.5 | 97.6 | 93.2 |
| 1.10 | 23 | 30.4 | 68.8 | 0.8 | 6.3 | 97.4 | 90.8 |
| 1.24 | 26 | 35.6 | 67.2 | 1.4 | 5.9 | 96.1 | 91.2 |
| 1.33 | 28 | 39.2 | 74.0 | 0.6 | 6.4 | 98.5 | 91.3 |
| 1.43 | 30 | 18 | 65.4 | 0.8 | 5.0 | 96 | 92.3 |
| 1.57 | 33 | 18 | 65.4 | 0.8 | 5.6 | 96 | 91.4 |
| 1.71 | 36 | 14 | 60.4 | 1.25 | 8.35 | 91% | 86 |
| 2.38 | 50 | 13.2 | 65.2 | 1.2 | 13.3 | 91% | 79.6 |

From the above results it can be seen that there was no effective increase in loss of cells per ml of harvest stream up to a perfusion rate of ~1.57 VVD.

Above this perfusion rate an increasing concentration of non viable cells could be observed within the harvest stream, with a decreasing total cell retention efficiency to 79.6% at 2.38 VVD. The viable cell retention also decreased, but to a lesser degree. This indicated that the settler device was able to perform as calculated for non-viable cells, with total cell retention below 21 dm$^3$ day, and breakthrough of smaller, non-viable cells above this flow rate.

We claim:

1. A device for separating particles from a bulk liquid under aseptic or sterile conditions, the device comprising means defining a plurality of settlement surfaces, the surfaces being inclined to the vertical, and means for causing liquid containing the particles to flow upwardly over said surfaces at such a rate as to allow particles to be separated from the bulk liquid to form sediment layers on the surfaces and slide down them, wherein said surfaces and said means for causing the liquid to flow upwards are contained within a sterile housing.

2. A device as claimed in claim 1, comprising at least fifteen settlement surfaces.

3. A device as in claim 1, wherein the means defining the settlement surfaces are plates.

4. A device as claimed in claim 3, wherein at least the uppermost surface of each plate is formed of mirror-polished stainless steel.

5. A device as claimed in claim 3, wherein the spacing between the plates is from 0.2 cm and 2 cm.

6. A device as claimed in claim 1, wherein the angle at which the surfaces are inclined to the vertical is from 10° to 50°.

7. A device as claimed in claim 1, wherein said vertically inclined settlement surfaces are mounted on a means for adjusting the angle of said incline, whereby the angle at which the surfaces are inclined to the vertical is adjustable.

8. A device as claimed in claim 7, wherein said means for adjusting the angle of said incline is an adjustable stand.

9. A device as claimed in claim 1, wherein the device is capable of being used at a liquid flow rate of from 0.5 to 5 dm$^3$/h.

10. A device as claimed in claim 1, wherein said housing is provided with an inlet for liquid containing particles to be separated, an outlet for liquid from which particles have been separated and a collection outlet for separated particles.

11. A device as claimed in claim 1, wherein the means for causing the liquid to flow upwardly over the settlement surfaces is a pump.

12. A device as claimed in claim 11, wherein the pump is capable of intermittent operation.

13. A device as claimed in claim 11, wherein the flow of liquid through the pump is capable of being periodically reversed.

14. A device as claimed in claim 1, said device further comprising temperature control means to keep the temperature of the liquid in the device within predetermined limits.

15. A device as claimed in claim 1, said device further comprising a collection outlet for removal of viable or total hybridoma cells from cell-containing medium.

16. A bioreactor apparatus, the apparatus comprising a fermenter vessel adapted to contain cells in liquid culture, and a device as claimed in claim 1 for operation under aseptic or sterile conditions, the device being so coupled to the fermenter vessel to allow cells, or a population of cells, in the liquid medium to be separated from liquid medium and returned to the fermenter vessel.

17. An apparatus as claimed in claim 16 wherein the fermenter is a stirred tank or airlift fermenter.

18. An apparatus as claimed in claim 16, which contains mammalian cells in liquid culture.

19. A process for separating particles from a bulk liquid under aseptic or sterile conditions, the process comprising causing liquid containing the particles to flow upwardly over a plurality of settlement surfaces, the surfaces being inclined to the vertical, at such a rate as to allow particles to be separated from the bulk liquid to form sediment layers on the surfaces and slide down them, said process carried out in the apparatus of claim 1.

20. A process as claimed in claim 19, wherein there are at least fifteen settlement surfaces.

21. A process as claimed in claim 19, wherein the settlement surfaces are defined by plates.

22. A process as claimed in claim 21, wherein at least the uppermost surface of each plate is formed of mirror-polished stainless steel.

23. A process as claimed in claim 21, wherein the spacing between the plates is from 0.2 cm and 2 cm.

24. A process as claimed in claim 19, wherein the angle at which the surfaces are inclined to the vertical is from 10° to 50°.

25. A process as claimed in claim 19, wherein said vertically inclined settlement surfaces are mounted on a means for adjusting the angle of said incline, whereby the angle at which the surfaces are inclined to the vertical is adjustable.

26. A process as claimed in claim 19, wherein the liquid flow rate is from 0.5 to 5 $dm^3/h$.

27. A process as claimed in claim 19, wherein the surfaces are contained in a housing provided with an inlet for liquid containing particles to be separated, an outlet for liquid from which particles have been separated and a collection outlet for separated particles.

28. A process as claimed in claim 19, wherein the liquid is caused to flow upwardly over the settlement surfaces by a pump.

29. A process as claimed in claim 19 wherein the temperature of liquid is kept within predetermined limits.

30. A process as claimed in claim 19 which comprises removing viable or total hybridoma cells from cell-containing medium.

31. A process of claim 19, wherein said bulk liquid is a liquid medium wherein mammalian cells are cultured.

* * * * *